United States Patent
Lohwongwatana et al.

(10) Patent No.: US 12,251,755 B2
(45) Date of Patent: Mar. 18, 2025

(54) ANTIMICROBIAL BIOCOMPATIBLE METAL ALLOY AND MANUFACTURE OF THE SAME

(71) Applicant: CHULALONGKORN UNIVERSITY, Bangkok (TH)

(72) Inventors: Boonrat Lohwongwatana, Bangkok (TH); Saran Tantavisut, Bangkok (TH); Chedtha Puncreobutr, Bangkok (TH); Thanawat Phetrattanarangsi, Nonthaburi (TH); Techawit Hirisatja, Nonthaburi (TH); Methawee Choosri, Nonthaburi (TH)

(73) Assignee: CHULALONGKORN UNIVERSITY, Bangkok (TH)

( * ) Notice: Subject to any disclaimer, the term of this patent is extended or adjusted under 35 U.S.C. 154(b) by 719 days.

(21) Appl. No.: 17/266,505

(22) PCT Filed: Aug. 6, 2019

(86) PCT No.: PCT/IB2019/056678
§ 371 (c)(1),
(2) Date: Feb. 5, 2021

(87) PCT Pub. No.: WO2020/058780
PCT Pub. Date: Mar. 26, 2020

(65) Prior Publication Data
US 2022/0088675 A1 Mar. 24, 2022

Related U.S. Application Data

(60) Provisional application No. 62/715,024, filed on Aug. 6, 2018.

(51) Int. Cl.
*B22F 1/052* (2022.01)
*A61L 27/10* (2006.01)
(Continued)

(52) U.S. Cl.
CPC .............. *B22F 1/052* (2022.01); *A61L 27/10* (2013.01); *A61L 27/306* (2013.01); *B22F 1/08* (2022.01);
(Continued)

(58) Field of Classification Search
CPC ......... A61L 2300/102; A61L 2300/404; A61L 27/06; A61L 27/10; A61L 27/306;
(Continued)

(56) References Cited

U.S. PATENT DOCUMENTS

| 2013/0309121 A1* | 11/2013 | Prest | B22F 10/25 219/121.64 |
| --- | --- | --- | --- |
| 2018/0339342 A1* | 11/2018 | Hofmann | B33Y 10/00 |
| 2018/0345366 A1* | 12/2018 | Hofmann | B22F 10/66 |

OTHER PUBLICATIONS

Thermal stability and mechanical properties of the TiCuZrPd glasses with 10, 14 and 20at%Pd (Year: 2014).*

(Continued)

*Primary Examiner* — Jenny R Wu
(74) *Attorney, Agent, or Firm* — WOMBLE BOND DICKINSON (US) LLP

(57) ABSTRACT

To provide Ti—Cu alloy formulations and additive manufacturing process configurations for fabrication of a bulk metallic glass (BMG) product that is biocompatible and antimicrobial, compositions of Ti-based metal alloy powder, comprising: Ti; Cu within a range of 5-30 atomic percent; transition metal within a range of 0-50 atomic percent, wherein such transition metal is one or a plurality of Zr, Nb, Ta, Pd, and Co, are disclosed. Moreover, additive manufacturing processes disclosed herein are capable of fabricating a bulk metallic glass of one or a combination of following phasic structures: fully amorphous microstructure; amorphous beta titanium phase; amorphous copper phase; and amorphous $(Ti,M)_2Cu$ phase. The resulting biocompatible
(Continued)

metal alloy product may be a medical device, particularly but not limited to a medical implant.

8 Claims, 9 Drawing Sheets

(51) Int. Cl.
    *A61L 27/30*     (2006.01)
    *B22F 1/08*     (2022.01)
    *B33Y 10/00*     (2015.01)
    *B33Y 70/00*     (2020.01)
    *B33Y 80/00*     (2015.01)
    *C03C 17/06*     (2006.01)

(52) U.S. Cl.
    CPC ............... *B33Y 10/00* (2014.12); *B33Y 70/00* (2014.12); *B33Y 80/00* (2014.12); *C03C 17/06* (2013.01); *B22F 2301/205* (2013.01); *B22F 2304/10* (2013.01)

(58) Field of Classification Search
    CPC .. A61L 27/54; B22F 1/052; B22F 1/08; B22F 1/09; B22F 10/28; B22F 10/36; B22F 10/366; B22F 10/64; B22F 2009/0824; B22F 2301/205; B22F 2304/10; B22F 2998/10; B22F 2999/00; B33Y 10/00; B33Y 70/00; B33Y 80/00; C03C 17/06; C22C 1/0458; C22C 14/00; C22C 2200/02; C22C 30/00; C22C 33/003; C22C 45/10; Y02P 10/25
    See application file for complete search history.

(56) References Cited

OTHER PUBLICATIONS

The novel toxic free titanium-based amorphous alloy for biomedical application Saran Tantavisut, Boonrat Lohwongwatana, Atchara Khamkongkaeo, Aree Tanavalee, Pairat Tangpornprasert, Pibul Ittiravivong (Year: 2017).*
A new Ti-based bulk glassy alloy with potential for biomedical application (Year: 2007).*
Novel Ti-based bulk metallic glasses with superior plastic yielding strength and corrosion resistance (Year: 2015).*
Investigation of glass-forming ability, deformation and corrosion behavior of Ni-free Ti-based BMG alloys designed for application as dental implants (Year: 2009).*
Glass forming ability and mechanical properties of Ti-based bulk glassy alloys with large diameters of up to 1 cm (Year: 2008).*

* cited by examiner

ANTIMICROBIAL BIOCOMPATIBLE METAL ALLOY AND MANUFACTURE OF THE SAME

TECHNICAL FIELD

The present invention relates to metal alloys used as a biocompatible material for medical purposes, particularly where the alloy exhibits antimicrobial properties. The present invention further relates to bulk metallic glass and its application to additive manufacturing processes.

BACKGROUND

Titanium (Ti) has been constantly regarded as an important component of metal alloys used for biomedical purposes, including uses in orthopedic applications, plastic surgery and neuro-surgery, etc. This is because of titanium's unique inherent properties: high strength-to-weight ratio, modulus and strength which are promisingly close to those of the bones, ability to be effectively sterilized, material workability, good corrosion resistance and excellent biocompatibility. There have been considerable attempts to improve the usefulness, or reduce the problems that may arise from the use of titanium-based alloy for biomedical purposes.

Infection is one of the main root causes of failed implants, being in constant contact with body fluids and tissues. To inhibit the microbial colonization that would lead to infection, several studies have investigated metals having antimicrobial properties and combinations thereof.

Copper (Cu) in its ionic form have been widely used as antimicrobial agents because of their excellent spectrum of antimicrobial properties. Copper ions' antimicrobial mechanisms are basically dissociation and release of relevant ions from the alloy structure or coating induced by the contact with bodily liquids or tissues (i.e. bio-corrosion).

Furthermore, additive manufacturing techniques (also known as 3D-printing) have been recognized as having many advantages compared to conventional manufacturing approaches, such as the ability to fabricate components with complex geometries and high material usage efficiency. Availability of several techniques under a shared concept and freedom to customize the process parameters give rise to great yet unexplored application possibilities, including for fabrication of medical devices.

CN 102943190 B discloses the addition of copper into a commercially-available medical titanium alloy Ti-6Al-7Nb, following with the heat treatment which forms the titanium-copper phase, mainly $Ti_2Cu$, which exhibits antimicrobial effects. Likewise, Zhang et al. (2016) provides a more comprehensive study into the nature of titanium-copper phase of a biomedical implant during the antimicrobial action, including the mechanical property and bio-corrosion. However, the formation techniques described therein are straightforward, and there is no discussion on the compatibility with more advanced manufacturing techniques, such as additive manufacturing.

US 20130309121 A1 discusses layer-by-layer construction methods of bulk metallic glasses which may apply to the fabrication of medical implants. Nonetheless, this publication lacks details about the fabrication process parameters and properties desired for a specialized implant, or antimicrobial effects.

U.S. Pat. No. 8,147,861 B2 discloses antimicrobial implants made of titanium alloys which are compatible with additive manufacturing techniques. The formulations described therein, however, are of titanium-silver alloys. This would incur a substantially greater cost than titanium-copper alloys in the commercial production.

Most recently, Deng et al. (2018) published an article on additive manufacturing using powder of $Ti_{47}Cu_{38}Zr_{7.5}Fe_{2.5}Sn_2Si_1Ag_2$, a known composition of Ti-based metal glass former. Although this work shows some promise for biomedical application, it suggests that further substantial experiments on the use of Ti-based glass-forming alloy with laser-based additive manufacturing techniques are needed until it may be reduced to industrial practice. Moreover, this publication does not discuss the antimicrobial property of additive-manufactured specimens.

An object of this invention is to address the foregoing technical gaps in the state of the art in order to provide antimicrobial, biocompatible metal alloys capable of satisfying the long existing demands.

SUMMARY OF THE INVENTION

It should be noted that the following Summary of the Invention, and later the Description of Preferred Embodiments, would serve only as illustrating examples of the concept of the present invention, and should not be interpreted in any way to limit such concept.

Pursuant to the foregoing background and object, the applicant found that the technical gaps in the state of the art may be because of (i) the lack of metal alloy composition and/or additive manufacturing process parameters capable of fabricating a bulk metallic glass (BMG) article of effective mechanical strength at a fast cooling rates that are typical of additive manufacturing techniques; and (ii) the lack of appreciation of the correlation between the degree of amorphousness/crystallinity of fabricated Ti-based alloy containing Cu ("Ti—Cu-based alloy"), and its antimicrobial property (in addition to mechanical strength), and the breadth of additive manufacturing techniques' process customization, which may be applied to customize the amorphousness of Ti—Cu-based alloy article and hence its antimicrobial property. The applicant further envisions that such customizable amorphousness and antimicrobial property provided by the concept of the present invention would provide much utility in the medical fields, particularly, invasive medical devices, such as implants and surgical tools. But the possible applications would of course not be limited to the medical fields, as it would as well apply to other industries that may benefit from the same technical advantages, such as accessories, and particularly body decoration (e.g. body-piercing).

The concept of the present invention relates to providing Ti—Cu-based alloy formulations and additive manufacturing process configurations such that the foregoing object, and the underlying technical problems, are addressed. Aspects of the present invention may include such formulations and process configurations, as well as the improvements to the biocompatible medical devices that are consequential to such formulations and configurations and are unforeseen in view of the state of the art. Enablement of all of these aspects requires the applicant's identification of technical problems (as stated above) and substantial experiments, and therefore is by no means obvious in the state of the art's perspective.

In a first aspect, embodiments in accordance with the present invention pertain to compositions of Ti—Cu-based alloy. Such compositions comprise Cu within a range of 5-30 atomic percent and transition metals within a range of 0-50 atomic percent, whereby the "transition metals" is one or a plurality of zirconium, niobium, tantalum, palladium and cobalt (Zr, Nb, Ta, Pd, and Co). Such compositions may be further characterized as having a relationship of Ti, Zr and Cu represented as $(Ti_{0.5+x}Zr_{0.5+x})_{100-y}Cu_y$, where x is within a range of 0-0.15 atomic percent; and y is within a range of 10-30 atomic percent. Moreover, such compositions may be further characterized as having a relationship of Ti, Zr, Pd, Cu, Co and Ta represented as $Ti_{44}Zr_{10}Pd_{10}Cu_{6+x}Co_{23-x}Ta_7$, where x is within a range of 0-8 atomic percent. Additionally, such compositions may be further characterized as having the relationship of Ti, Cu, Zr and other transition metals represented as $Ti_xCu_yZr_zQ_a$, where Q is one or a plurality of the other transition metals (Nb, Ta, Pd and Co); and where x is within a range of 60-70 atomic percent; y is within a range of 15-20 atomic percent; z is within a range of 5-10 atomic percent and a is within a range of 0-10 atomic percent.

The above embodiments are capable of providing a good biocompatibility with bone because of the low modulus of elasticity as a result of amorphous phase in the matrix of fabricated BMG article. Further, the above embodiments are as well capable of providing Cu-containing phases (e.g. amorphous, elemental copper phase, precipitate) that is capable of releasing copper ions (i.e. being corroded) at a desirable rate that is sufficiently slow to preserve the BMG structure so as to achieve the intended lifecycle, while at the same time sufficiently fast to provide an antimicrobial action so as to effectively prevent the infection.

Furthermore, the above embodiments are capable of being worked into a BMG article having any one or combination of the following structures: (i) fully amorphous microstructure; (ii) amorphous and beta Ti phase; (iii) amorphous and elemental Cu phase; and (iv) amorphous and $(Ti,M)_2Cu$ phase, where M could be one or a plurality of the other transition metals (Zr, Nb, Ta, Pd and Co). Customization of such phases may be carried out by means in accordance with another aspect of the present invention.

In a second aspect, embodiments in accordance with the present invention pertain to an additive manufacturing process of certain parameters. Such additive manufacturing process is capable of fabricating a BMG article having any one or combination of the following structures: (i) fully amorphous microstructure; (ii) amorphous and beta Ti phase; (iii) amorphous and elemental Cu phase; and (iv) amorphous and $(Ti,M)_2Cu$ phase, where M could be one or a plurality of the other transition metals (Zr, Nb, Ta, Pd and Co). By configuring certain process parameters, such additive manufacturing process is further capable of customizing the amount of amorphous phase(s) at any location of the BMG article, as well as further capable of customizing the microstructure at any location of the BMG article. Said control of microstructures provides capability to control the rate at which Cu-ions are released during the intended use of BMG article. And by the foregoing "any location of the BMG article", the respective customizations per the embodiments may be performed at the BMG article's core, surface, or anywhere in between.

Embodiments per the second aspect may be performed in connection with (i) any existing Ti—Cu-based alloy composition; or (ii) Ti—Cu-based alloy powder of any distribution of particle sizes or shapes; or (iii) Ti—Cu-based alloy powder provided by any means of preparation; or (iv) with or without any post-fabrication heat treatment, and still capable of fabricating a BMG article that is in accordance with the concept of the present invention.

Regardless, the applicant found that the second aspect is preferably performed in connection with (i) a Ti—Cu-based composition that is in accordance with the first aspect; and/or (ii) Ti—Cu-based alloy powder having spherical shape with mean particle size in a range of 10-100 μm; and/or (iii) Ti—Cu-based alloy powder prepared by a 3d-rotational mixing method; and/or (iv) with post-fabrication heat treatment.

In a third aspect, embodiments in accordance with the present invention pertain to biocompatible metal alloy products resulting from compositions and/or additive manufacturing processes in accordance with the first and/or second aspect. Such products are in particular, but not limited to, medical devices, and more particularly medical implants.

DETAILED DESCRIPTION OF PREFERRED EMBODIMENTS

Figure 1:
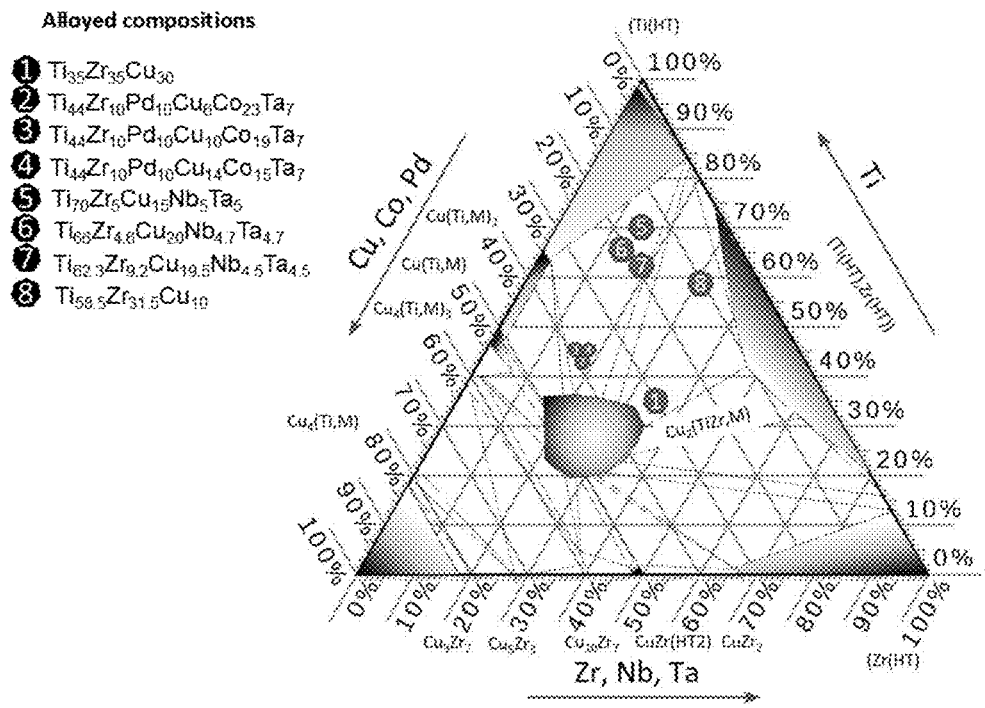
FIG. 1 shows a pseudo equilibrium ternary phase diagram of different compositions of alloys per preferred embodiments.

Aspects and embodiments in accordance with the present invention are directed to providing biocompatible Ti-based alloys capable of exhibiting antimicrobial and bone-like mechanical properties. As previously noted, the embodiments may be applied to fabrication of any products which may benefit from such properties; for the purpose of this Detailed Description, however, the embodiments will be discussed mainly in relation to medical implants.

More particularly, the aspects and embodiments are directed to fabricating an article of alloy which may be characterized as bulk metallic glass (BMG). Unless indicated otherwise, "bulk metallic glass" or "BMG" is herein intended to mean an article formed of a metal alloy system, such article having an amorphous structure of various print dimensions. Though in specific metallic glass community, BMG is only limited to a group of glassy metals that could be cast at least 2 mm thick ('casting thickness') to achieve fully amorphous structure. Such minimum thickness may be increased in this publication as the parts could be 3D printed into larger dimension.

The antimicrobial effect comes predominantly from copper ions as they are released into certain bodily fluids. The release rates of copper ions depend on the four main parent phases: amorphous phase, $Ti_2Cu$ phase, elemental copper phase, and $(Ti,M)_2Cu$ phase, M being one or more alloying element selectable from the group of previously mentioned transition metals: Zr, Nb, Ta, Pd and Co. Phase segregation of copper is observed in amorphous phase both during heat treatment, and later inside bodily environment. Such phase segregation will help control the release of copper from amorphous phase, while chemical reactions and chemical gradient may drive release of copper ions from metallic copper islands (clusters) and/or intermetallic compounds. Other elements, such as Palladium (Pd), also exhibit antimicrobial effects with relatively different degrees of cellular responses. The bone-like mechanical property comes predominantly from amorphous phase that exhibits relatively low modulus of elasticity (more similar to natural bone property). The beta titanium phase (β-Ti) may also be preferably included in the microstructure to improve ductility and change in elastic Young's modulus Therefore, various metal elements were selected for alloy systems per the concept of present invention.

Titanium (Ti) with good biocompatibility and mechanical properties was chosen as base metal. Copper (Cu) was chosen predominantly for antimicrobial effect. Transition metals were chosen to enhance glass forming ability for amorphous formation. Among numerous transition metals that may be applicable to the concept of the present invention, a group comprising Zirconium (Zr), Niobium (Nb), Tantalum (Ta), Palladium (Pd), Cobalt (Co) is preferred. The chemical compositions (hereinafter, in term of atomic percentage) of such alloy systems comprises copper within a range of 5-30 atomic percent and transition metal within a range of 0-50 atomic percent. The transition metal may be one or a plurality of the abovementioned Zr, Nb, Ta, Pd and Co.

Aspects of the present invention are particularly compatible with rapid solidification (which is a consequence of fast cooling rate) typically found in laser-based additive manufacturing techniques or surface coating. These aspects, alone or in combination, provide means for fine tuning the following microstructures
Fully amorphous microstructure
Amorphous and beta titanium phase
Amorphous and elemental copper phase
Amorphous and $Ti_2Cu$ and/or $(Ti,M)_2Cu$ phase, M being one or more alloying element selectable from the group of previously mentioned transition metals: Zr, Nb, Ta, Pd and Co. Specific examples of $(Ti,M)_2Cu$ phase include $(Ti_{0.4}Zr_{0.4}Nb_{0.2})_2Cu$. Moreover, $(Ti,M)_2Cu$ covers a tolerance of $(Ti,M)_{2\pm0.2}Cu$ phase as well. The atomic ratio of Ti (or M) to Cu is approximately within a range of 1.8:1 to 2.2:1.

Although the additive manufacturing process per the embodiments alone may produce the microstructure needed in an as-printed state, some heat treatment after the step of additive manufacturing is preferred. The heat treatment could be done both in-situ during additive manufacturing and post additive manufacturing. With customization of microstructure, the release of copper in bodily fluid could be tailor-made.

Alloy Compositions

Preferred alloy compositions in accordance with the concept of present invention are shown by way of example in Table 1. Additionally, FIG. 1 shows a pseudo equilibrium ternary phase diagram with different compositions of the alloys that could generate any one or combination of the following structures: (i) fully amorphous microstructure, (ii) amorphous and beta titanium phase, (iii) amorphous and elemental copper phase, and (iv) amorphous and $(Ti,M)_2Cu$ phase.

TABLE 1

Examples of preferred alloy compositions

| Alloy No. | Composition (atomic percent) | | | | | | |
|---|---|---|---|---|---|---|---|
| | Ti | Cu | Zr | Nb | Ta | Pd | Co |
| 1 | 35 | 30 | 35 | — | — | — | — |
| 2 | 44 | 6 | 10 | — | 7 | 10 | 23 |
| 3 | 44 | 10 | 10 | — | 7 | 10 | 19 |
| 4 | 44 | 14 | 10 | — | 7 | 10 | 15 |
| 5 | 70 | 15 | 5 | 5 | 5 | — | — |
| 6 | 66 | 20 | 4.6 | 4.7 | 4.7 | — | — |
| 7 | 62.3 | 19.5 | 9.2 | 4.5 | 4.5 | — | — |
| 8 | 58.5 | 10 | 31.5 | — | — | — | — |

Per the above Table 1, Alloy 1 and Alloy 8 may be represented as $(Ti_{0.5+x}Zr_{0.5+x})_{100-y}Cu_y$, wherein x is within a range of 0-0.15 atomic percent and y is within a range of 10-30 atomic percent On the other hand, Alloys 2, 3 and 4 may be represented as $Ti_{44}Zr_{10}Pd_{10}Cu_{6+x}Co_{23-x}Ta_7$, wherein x is within a range of 0-8 atomic percent. In addition, alloys 5, 6, and 7 may be represented as $Ti_xCu_yZr_zQ_a$, wherein Q is one or a plurality of the other transition metals (Nb, Ta, Pd and Co); x is within a range of 60-70 atomic percent; y is within a range of 15-20 atomic percent; z is within a range of 5-10 atomic percent and a is within a range of 0-10 atomic percent.

Preparation of Alloy Powder

According to the concept of present invention, the foregoing alloy compositions are preferably used in their powdered form. Such powder may be prepared by way of pre-alloyed powder or blended powder, among others.

The pre-alloyed powder involves a process, usually melting, to obtain an ingot that having target alloy composition and a subsequent process, preferably gas-atomization, to turn this ingot into powder alloy with chemical homogeneity. Particularly, the pre-alloyed powder consists of a plurality of particles, each one having the same composition.

Alternatively, blended (i.e. pre-mixed) powder could be prepared by a process to intermix elemental powders (e.g. Ti, Cu, Zr, Ta, Pd, Co). Preferably, such powder comprises particles having a size within a range of 10-100 μm and a generally spherical shape. The pre-mixing process in accordance with preferred embodiments is novel in a way that no ball/bead is required in the pre-mixing container. As a result, higher purity of powder and lower contaminants (e.g. iron or carbon elements/compounds originating from such ball or bead) may be achieved. In order to achieve a preferable homogeneity, a rotational pre-mixing equipment with simultaneous 3-axis rotation is preferred. Preferably, the pre-mixing is carried out in a range of 5-30 rpm rotational speed with a pre-mixing time of 2-6 hours. The pre-mixing is as well preferably operated under Argon protective atmosphere to minimize level of oxygen, nitrogen and hydrogen contamination. Particularly, the mean composition of the blended powder after the completion of pre-mixing is within the target alloy composition, but the adjacent particles may have variation in their compositions and sizes.

Figure 2:
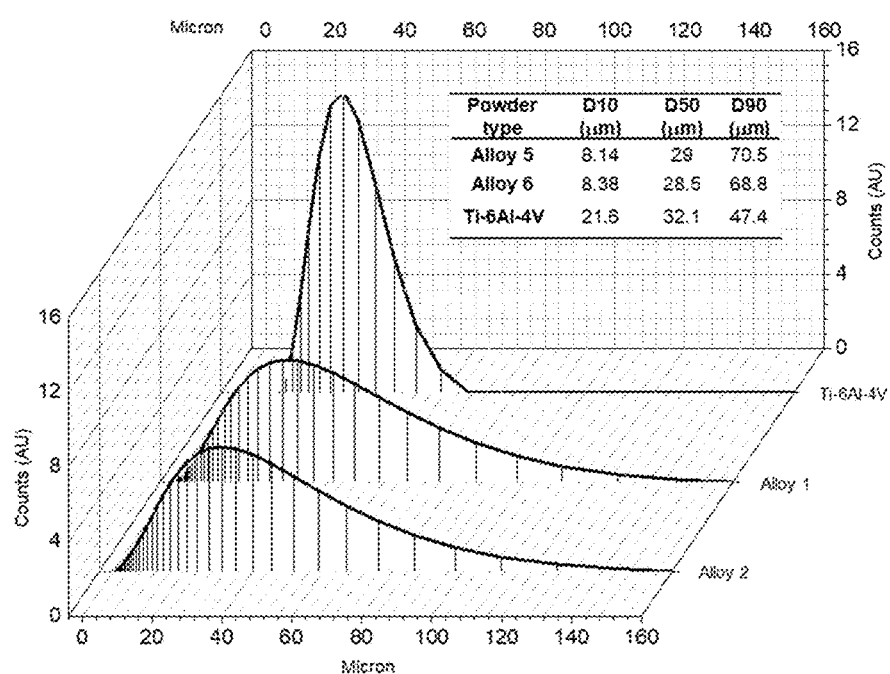
FIG. 2 shows powder size distribution per preferred embodiments.

For example, a batch of titanium elemental powder was intermixed with a batch of copper and zirconium elemental powders. Other alloying elements at proper ratios may be added to fine-tune the microstructure that is relevant to the release of copper ions. The intermixed powder will be used as raw material in a powder bed technique. The powder parameters, including but not limited to, (1) size distribution, (2) shape, (3) oxygen content, and (4) elemental or alloyed compositions, are important considerations. In FIG. 2, as an example, particle size distributions of two mixtures of elemental powder (indicated as "Alloy 5" and "Alloy 6") are shown in comparison with the narrower distribution of commercially available Ti-6Al-4V alloyed powder. Ti-6Al-4V size distribution has been used to produce >99.95% density 3D printed parts in our test. For the intermixed alloys, the powders were mixed together so that the size distributions were purposely different. The measurement was done in laser diffractometer particle size analyzer according to ASTM B822-10. The values for D10, D50 and D90 of Ti-6Al-4V powder are 21.6 microns, 32.1 microns and 47.4 microns respectively.

Figure 3:
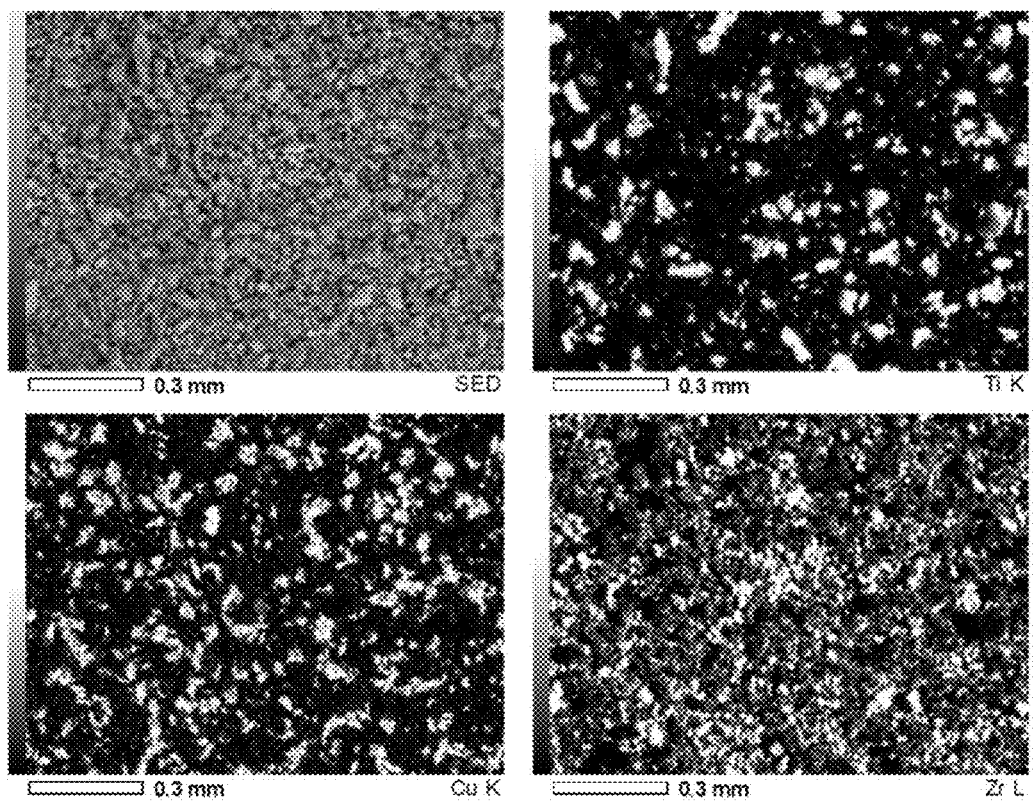
FIG. 3 shows particle distribution and elemental mapping image of Alloy 1 of a preferred embodiment.

To properly control the rapid solidification process, the size distributions and shape of each elemental powders were carefully selected to correlate with laser parameters and scan strategy. In one example of the present invention, the geometry of the elemental powders was not in the spherical shape, but the mixing process could still provide good particle distribution and chemical homogeneity (i.e. elemental mapping) of the three elemental powders as shown in a scanning electron microscope (SEM) image of FIG. 3.

Fabrication by Additive Manufacturing

Powder prepared in accordance with the above embodiments are then used as raw materials for additive manufacturing process, whereby an intended article is fabricated in a layer-wise manner. Here, the preferred varieties of additive manufacturing techniques are power-bed laser melting techniques, including so-called selective laser melting (SLM).

In SLM, each cross-section of the component is built by means of consecutive scan of the laser beam to fully melt and fuse metallic powder. The characteristics of SLM process are fully melting and rapid solidification of metal as a result of small interaction volume and short interaction time between high-energy laser beam and material. This rapid solidification (cooling rates ranging between $10^3$-$10^8$ K/s) makes it suitable for the formation of amorphous metal. The cooling rate, as well as the resulting microstructure, can be tailored at any point within the component by controlling the processing parameters such as laser power, scan speeds, hatch spacing, layer thickness and scanning strategy.

The laser power may be selected so that the powder melts completely and homogeneously throughout the layer thickness. To manufacture the alloys in accordance with the present invention, the laser power is preferably at least 50 Watt.

Thickness of each powder layer may be determined from the particle size and applied laser power. According to the preferred embodiments, such layer thickness is within the range of 30-60 μm.

The scan speed and hatch spacing may be selected to facilitate the solidification conditions for the formation of amorphous metal and $Ti_2Cu$ phase. As discussed in alloy-design section, amorphous metal would result in a lower modulus of elasticity, and $Ti_2Cu$ phase would be beneficial for antimicrobial response According to the preferred embodiments, such scan speed is within a range of 65-2,000 mm/s, and such hatch spacing is within a range of 0.07-0.15 mm.

Even more preferably, the foregoing parameters may be adjusted so that the level of amorphousness and the amount of $Ti_2Cu$ phase are tailored for specific locations of the same article. For example, the additive manufacturing process may be configured such that two set of parameters are used for (i) the core and (ii) the surface of the same article. This is to promote antimicrobial response at the surface while maintaining appropriate modulus of elasticity at the core of same article.

The abovementioned processing parameters are directly related to energy density which determines not only the cooling rate but also the flow of liquid metal in the melt pool and heat affected zone (HAZ). High energy density leads not only to a high cooling rate, but also to a stronger chemical inhomogeneity (negatively affect amorphous formation) and larger HAZ. Thermodynamics modelling and finite element analysis of heat transfer may be used to identify potential processing parameters for experimental observation.

Scanning strategy may also be selected to accommodate homogeneous distribution of the constituent elements as well as heat transfer. A strategy having scanning vectors with 67-degree or 90-degree rotation in adjacent layers and scanning twice in each layer is preferred in order to promote a homogenous and amorphous microstructure.

Finally, heat treatments could be done either in-situ (i.e. during the additive manufacturing process) or post additive manufacturing to further promote the formation of copper-containing precipitates for antimicrobial property. The temperature of the heating plate may be in a range of 80-200° C. for in-situ heating. For the post additive manufacturing heat treatment, conditions with a temperature range of 790-950° C. and isothermal holding for 1-2 hours may be applied to the alloys.

EXAMPLE

Figure 4:
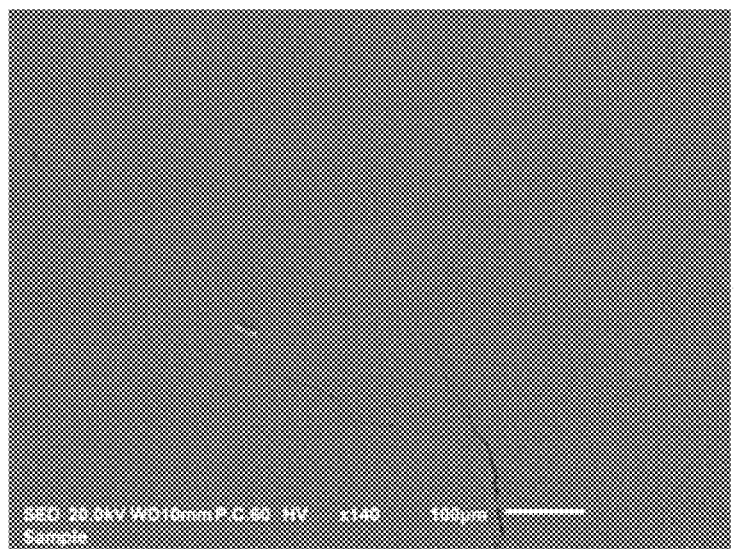
FIG. 4 shows a micrograph of $Ti_{38}Zr_{35}Cu_{30}$ alloy per a preferred embodiment.
Figure 5:
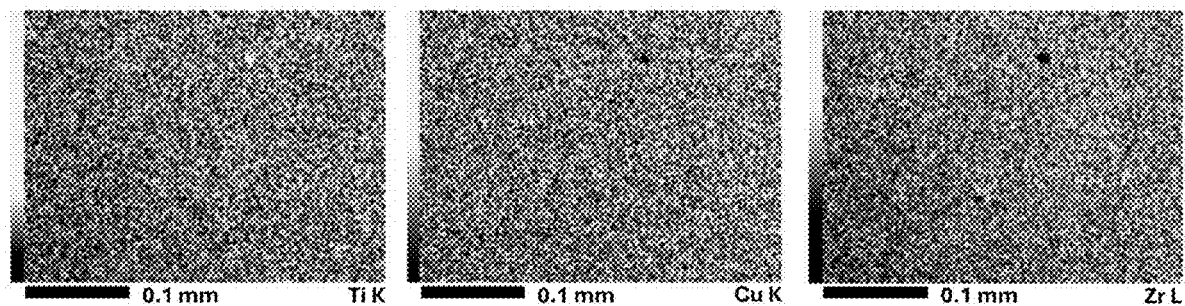
FIG. 5 shows a micrograph of elemental mapping of $Ti_{35}Zr_{35}Cu_{30}$ alloy per a preferred embodiment.

Alloy No. 1 per Table 1 above, having a composition of $Ti_{38}Zr_{35}Cu_{30}$ (atomic percent), was prepared as blended powder and was fabricated using the following SLM processing parameters: The laser power of 95 W, scanning speed of 100 mm/s, hatch spacing of 105 μm and layer thickness of 40 μm. Scanning vectors with 90-degree rotation in adjacent layers and scanning twice in each layer were applied. The results from scanning electron microscopy (SEM), as shown in FIG. 4, illustrates that a homogenous and amorphous as-built microstructure could be achieved. In addition, FIG. 5 demonstrates good homogeneous distribution of the constituent elements in the as-built microstructure. This observation confirms the efficiency of powder mixing and selective laser melting processes to fabricate an alloy per the preferred embodiments.

Figure 6:
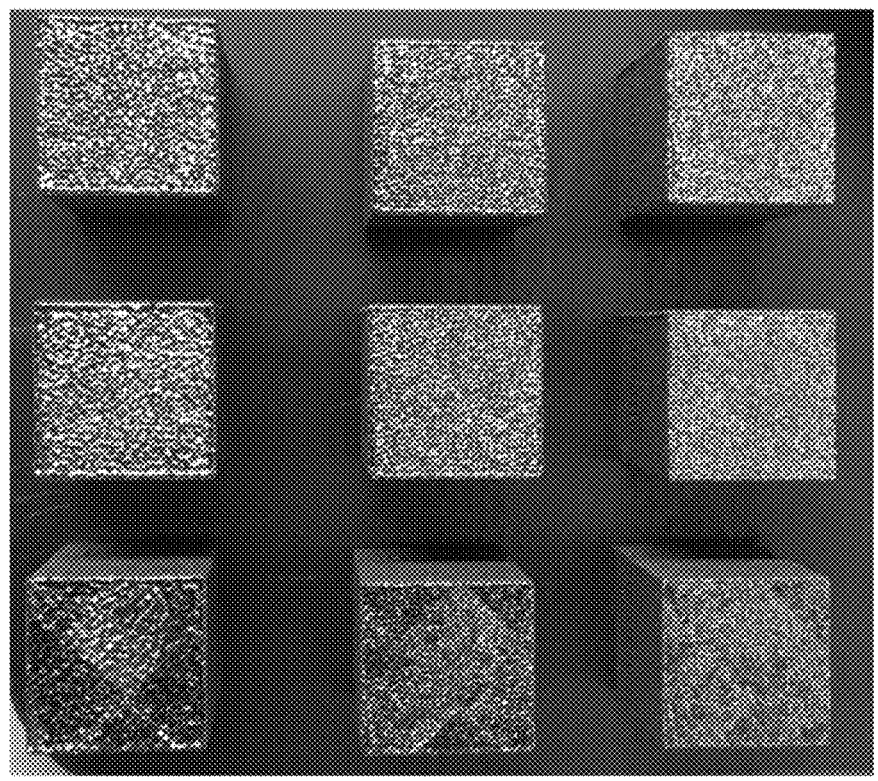
FIG. 6 shows test platforms for cubes 3D-printed with different scan strategies to control local topology.

Verification of Amorphization 3D-printed articles could be fabricated with different processing parameters and scan strategies so as to control the formation of beta titanium phase (P—Ti), $Ti_2Cu$ and $(Ti,M)_2Cu$. FIG. 6 Shows samples of different build volume that were printed on the platform in different configurations. Notice the different build topologies created by scan strategies. As part of our invention, the surface is fine-tuned so that there are local areas of metastable phase formation that could be tailored towards antimicrobial property.

According to an X-ray diffractometry (FIG. 7A), scanning electron micrography (SEM) combined with energy dispersive x-ray spectrometry (EDX) and transmission electron micrography (TEM) were used to identify various phases such as: fully amorphous microstructure, amorphous and beta titanium phase, amorphous and elemental copper phase, and amorphous and $(Ti,M)_2Cu$ phase. SEM micrographs and EDX analysis revealed local areas where $Ti_2Cu$ is located as shown in FIG. 7B and FIG. 7C.

The samples were confirmed to be amorphous in selected area diffraction technique in TEM. X-ray diffraction was used to confirm the amorphous fraction in the as-printed and heat treated specimen. For good glass formers like Alloy 2, Alloy 3, and Alloy 4, the as-printed parts were fully amorphous.

Figure 7A:
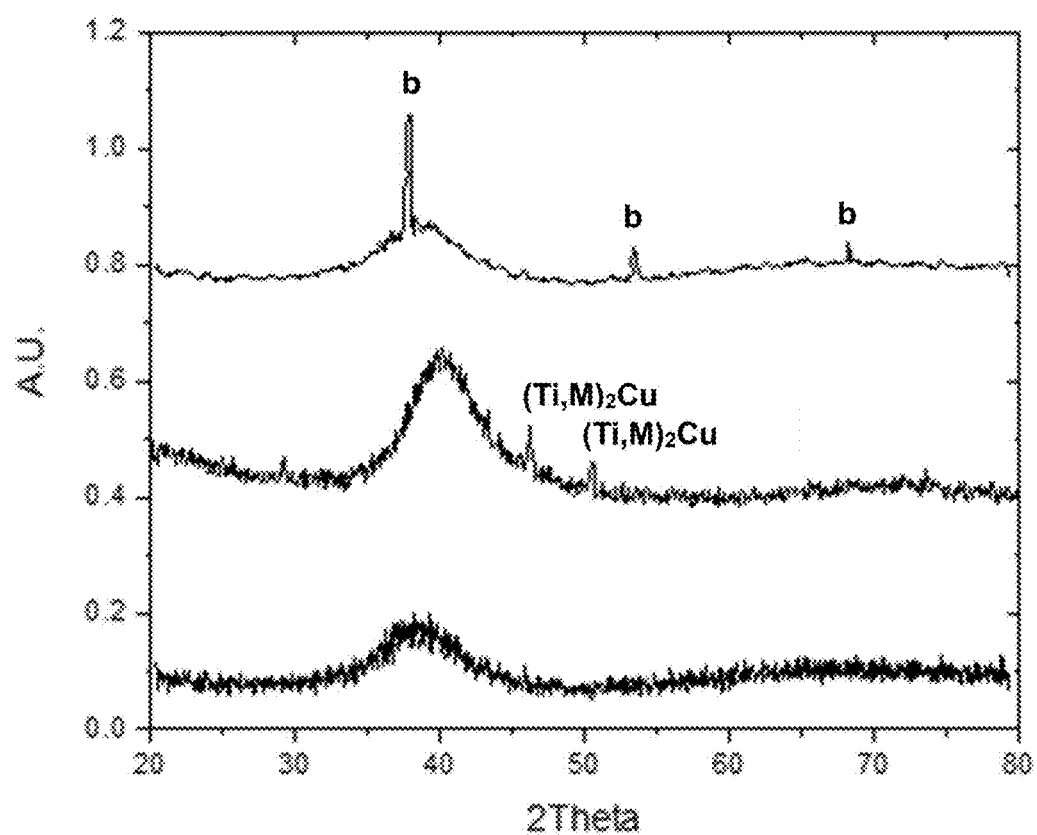
FIG. 7A shows X-ray diffraction patterns for alloy that was found fully amorphous (bottom graph), partially amorphous decorated with $(Ti,M)_2Cu$ crystals (middle graph) and partially amorphous decorated with beta-titanium (top graph).
Figure 7B:
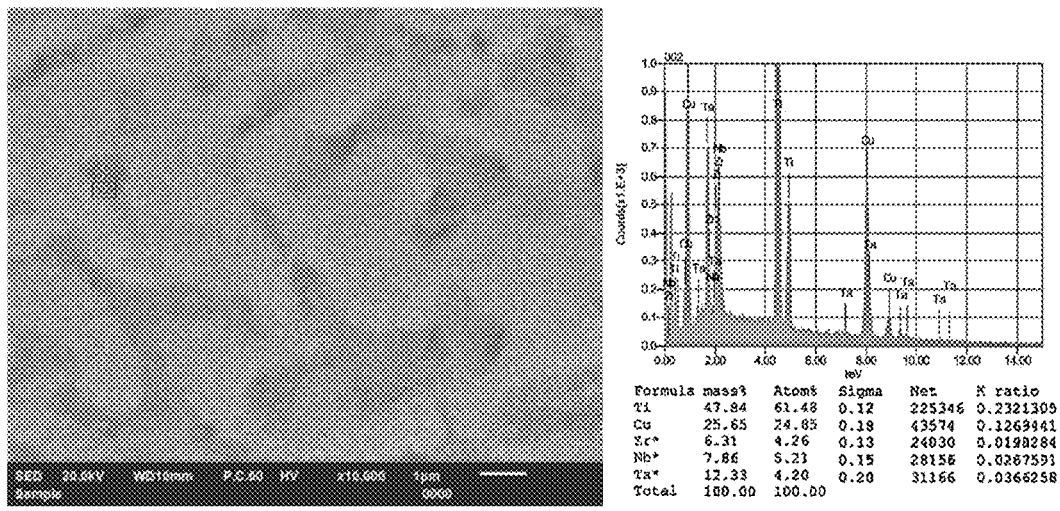
FIG. 7B shows SEM micrograph indicates the EDX point scan which revealed the area where $Ti_2Cu$ is located. The inclusion phase is of the order 1-3 microns and scattered throughout the printed samples.
Figure 7C:
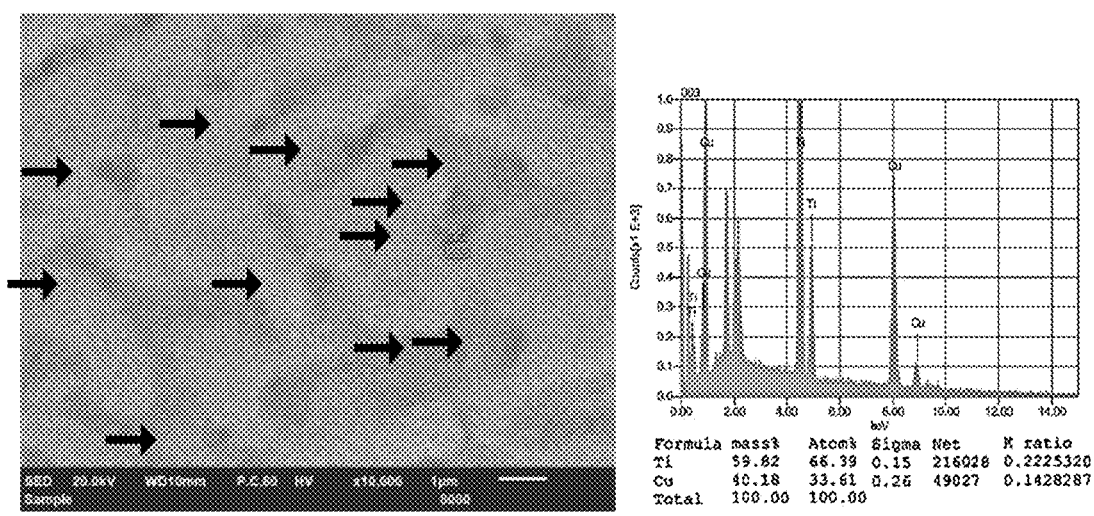
FIG. 7C shows SEM micrograph indicates the EDX point scan which revealed other locations where $Ti_2Cu$ inclusions are located (black arrows). The inclusion phase is of the order 1-3 microns and scattered throughout the printed samples.

The control of laser parameters and scan strategies could affect the melt pool which thereby limits copper diffusion, and combine such with proper heat treatment profile, some of the crystals could be formed towards our anti-microbial application as shown in FIG. 7A. The middle graph shows inclusions of $(Ti,M)_2Cu$ crystals for the compositions centered around Alloy 5. The top graph shows later crystallization of beta-titanium phase which could be beneficial to the mechanical property to match better with human bone.

The values for elastic Young's modulus are approximately 8-24 GPa of cortical or solid bone. The scattered values are due to the completeness of the tests such as wet bone test, four-point bending test, three-point bending test of complex structure of combined cortical and trabecular bone, and ultrasonic test. For Ti-6Al-4V alloy, the elastic Young's modulus is of the order 113-125 GPa depending on test geometry and measurement techniques. For our cases, ultrasonic sound velocity measurement was employed on several Ti—Cu-based alloys and the elastic Young's moduli were in the range between 76-102 GPa. Examples include 81+/−3.2 GPa of combined amorphous and beta Ti/Ta phase for $Ti_{40}Zr_{15}Cu_{30}Nb_8Ta_7$ alloy after heat treatment, and 79+/−4.5 GPa for $Ti_{60}Zr_{17}Cu_{18}Pd_{10}$ after heat treatment.

Cytotoxicity and Positive Biological Responses with Cells

Figure 8:
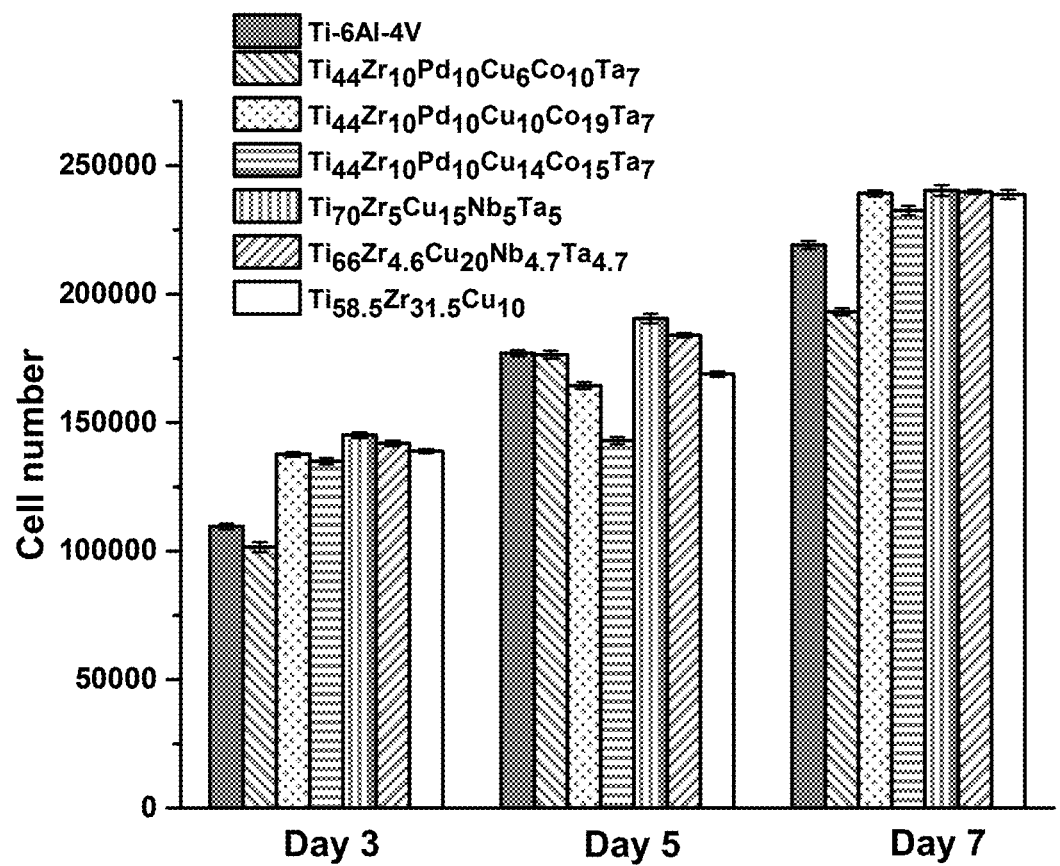
FIG. 8 shows MTT Assay which was completed for six new alloys with one controlled alloy (Ti-6Al-4V). Cells show viability and the cellular counts suggest proliferation capability.
Figure 9:
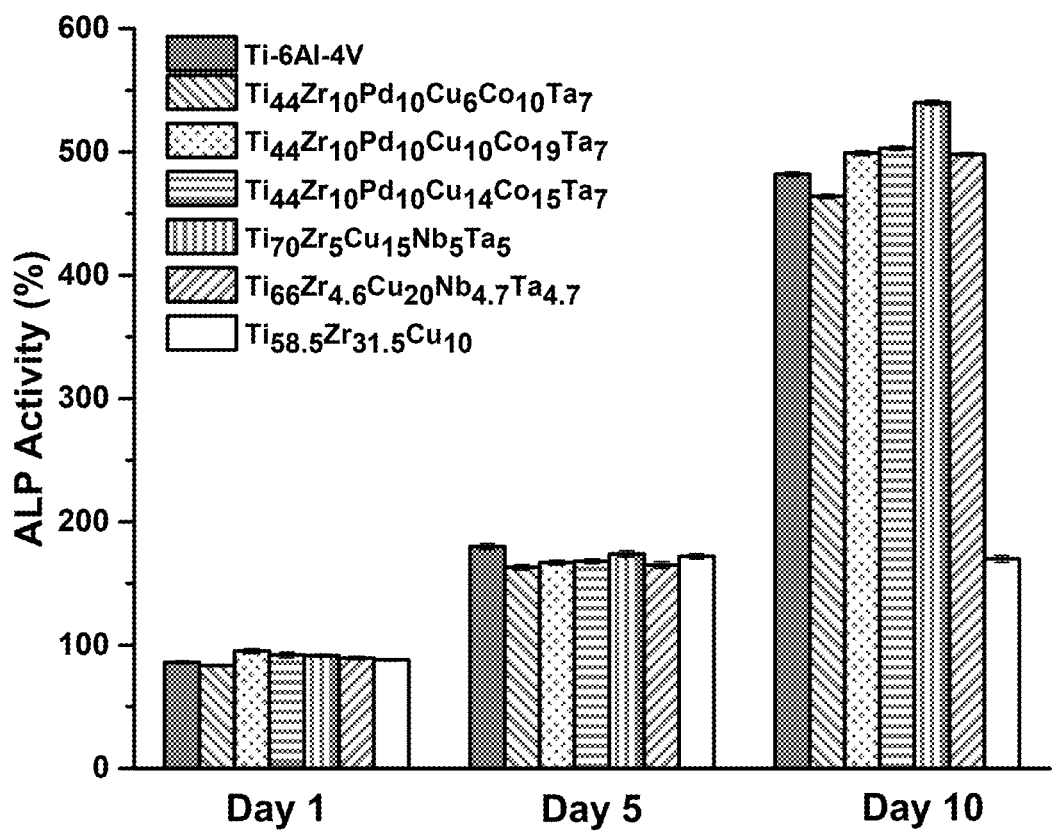
FIG. 9 shows ALP activities which were measured for series of alloy compositions at Day 1, Day 5 and Day 10.

Cytotoxicity evaluation was performed according ISO/EN 10993 part 5 as well as other methodologies related as extensions. Direct contact assays were done by using a cell line of human osteoblast like cells: SaOS-2. Osteoblastic cell line, SaOS2 or Sarcoma osteogenic, were used for in-vitro studies. After obtaining the cell line from cryopreserve vial, the cells were suspended in fresh medium then incubated in incubator supplied with 5% $CO_2$, 95% $O_2$ at 37° C. At 5 days after thawing process, the photo was taking at confluency around 90% to show cell vitality. MTT assay is a colorimetric assay technique to assess the metabolically active cellular activities. The indicator involves the reducing of a yellow tetrazolium-based compound to a purple formazan product. As the number of living cells in the culture is directly related to the quantity of formazan product, the number of living cells may be quantified by the absorbance at 570 nm of wavelength. After cells were exposed to the surface for 3 days, 5 days and 7 days, no difference was detected when compared to the control as a screening method for cytotoxicity. The tests were repeated for many alloy recipes. Shown in FIG. 8, six compositions were compared to show that in 7 days, there was no sign of cell cytotoxicity. The same test was repeated on MC3T3 and the results were comparable in both cellular responses. Cell viability assays (MTS test) also revealed that cells were viable after two weeks in culture. As shown in FIG. 9, alkaline phosphatase (ALP) activity was higher in the supernatants collected from the pre-mineralized samples when compared to the control samples.

Antimicrobial Effects

Figure 10:
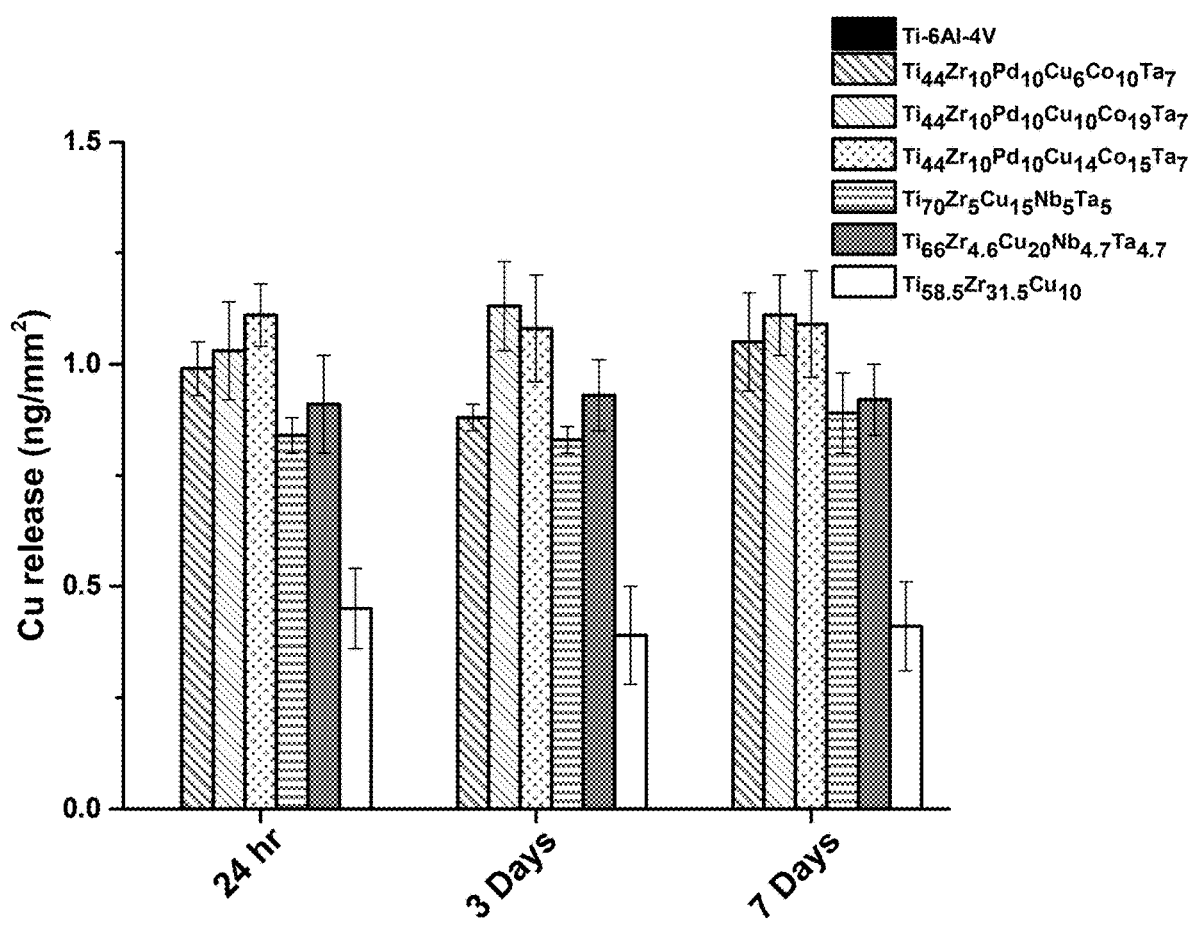
FIG. 10 shows copper release which was monitored via ICP method. Different alloy compositions have different rates of copper release into simulated bodily fluid.

Copper release test was carried out following ISO 10993-12 and ISO 10993-15. The printed specimens were soaked in NaCl solution at 0.9 weight percent concentration at 37° C. for one day. The surface area/volume ratio was kept constant at 15 $cm^2/cm^3$. The solution was then tested for the release of Cu, using Inductively Coupled Plasma Spectrometry (ICP-MS) to measure the copper release. The results are shown in FIG. 10.

Figure 11:
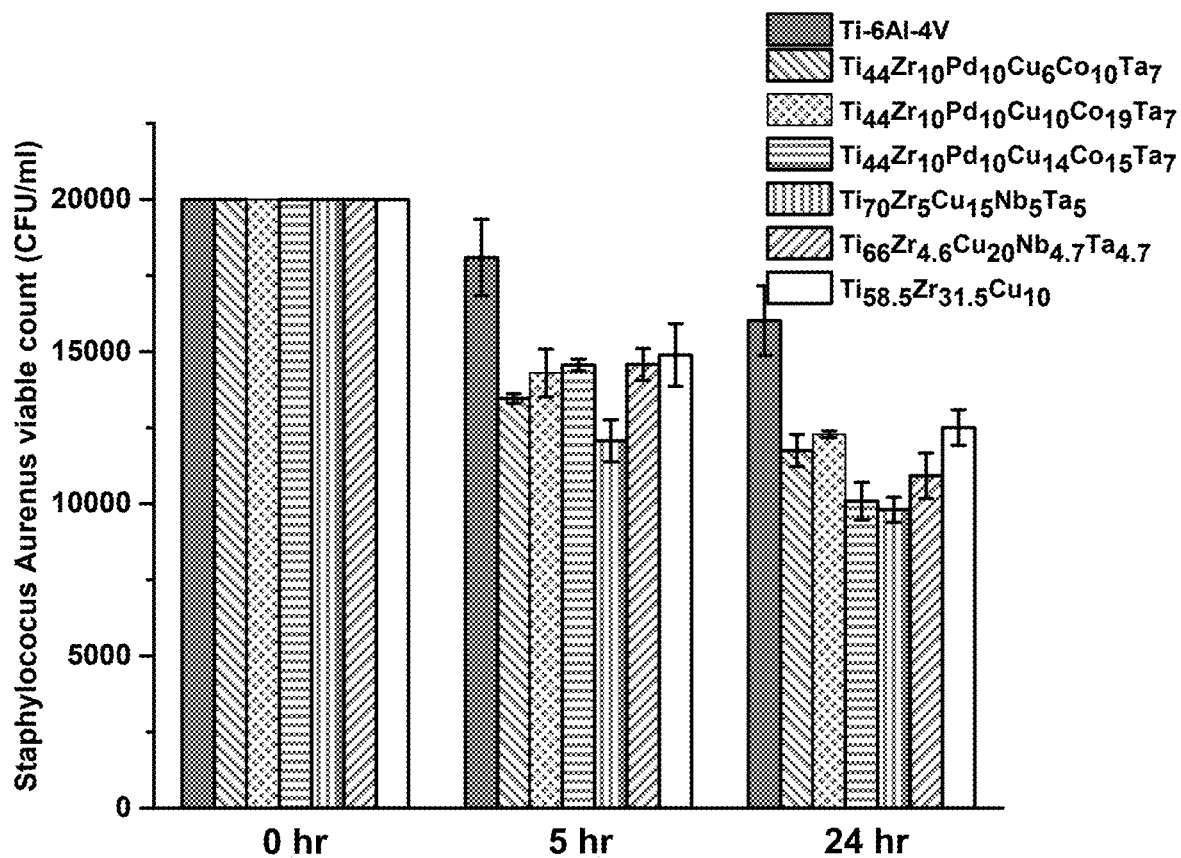
FIG. 11 shows *Staphylococcus aureus* which is common in bone related infection. The test was to monitor the reduction in colony forming unit counts. For all different species of the alloys. Shown as examples here, the alloys could help reduce the CFU counts in 24 hours and have the tendency to work in longer terms.

To test antimicrobial property of the alloy surface, *Staphylococcus Aureus* strain was used as test subject to observe and count the colony forming units (CFU). First, all samples were autoclaved, then placed in 15 cc Falcon tubes containing MH broth. The tubes were inoculated with 20,000 CFU/ml *S. aureus*. The tubes were then incubated at 37° C. for 48 hours on a rocking table at 12 cycle/min. Samples were then removed from the original tubes, and rinsed with saline solution to remove planktonic cells. The specimens were then placed into new tubes with MH broth. Next, the tubes were sonicated to detach biofilm before being incubated again at 37° C. The samples were then transferred to MH agar plate and counted for CFU at specified time periods. The results are shown for the periods of 5 hours and 24 hours in FIG. 11.

The CFU/ml of *Staphylococcus Aureus* in control specimen were significantly higher than the counts in all new alloys (p value <0.02 in all cases), indicating an improved antimicrobial effect. It must be noted that there are several proposed methods for anti-microbial property. One evaluation is known as disk diffusion method using Mueller Hinton agar. The antibacterial activity of the material is controlled by diffusion in media and the zone of inhibition could be recorded. This method provides direct to surrounding diffusion measurement but requires rigorous dissolution of ions from the metal and diffusion through stationary agar. With clinical trials, it is known that blood supplies will circulate and affect the infection. Therefore a more dynamic test involving bodily fluid movement is more preferred.

Figure 12:
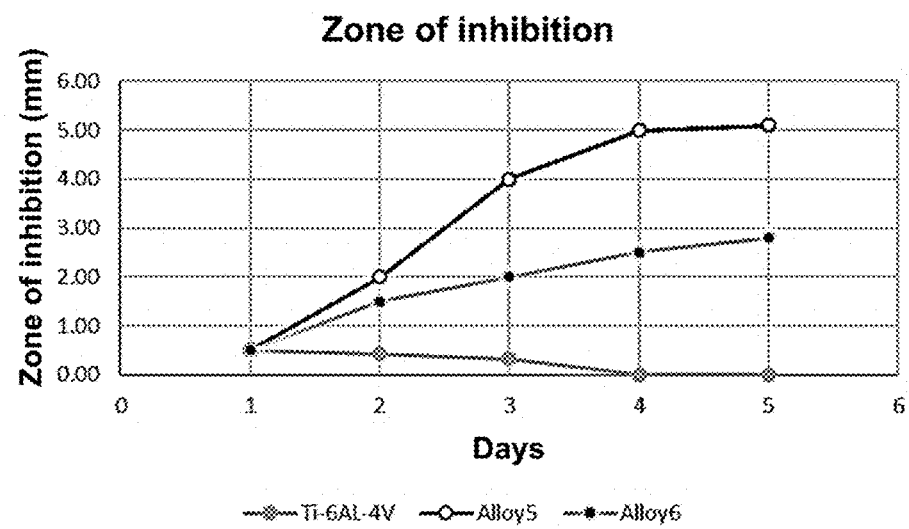
FIG. 12 shows the zone of inhibition of *Staphylococcus aureus* in agar gel tested with two alloys, Ti-6Al-4V being used as benchmark.

One long term anti-microbial strategy is based on the ability to prolong the release copper ions on a daily basis for at least 1-2 weeks, such as shown in copper release test. This is a critical time in which patient has a high risk for infection. As it was demonstrated with a simple geometry, the release of copper could be prolonged and maintained at least for one week for persistent microbial effect. More complex geometry could be further created to match with required copper release amount via geometrical correlation with the surface area as long as the level of copper release could be matched with locally required dose. The zone of inhibition is shown in FIG. 12 to demonstrate long term anti-microbial effects of two example alloys per the embodiments (Alloy 5 and Alloy 6 per Table 1 above), in comparison with the benchmark specimen (Ti-6Al-4V).

The invention claimed is:

1. A Ti-based metal alloy powder, consisting of:
Ti;
Cu within a range of 5-30 atomic percent; and
transition metal within a range of 0-40 atomic percent,
wherein such transition metal is one or a plurality of Nb, Ta, Pd, and Co, a combined range of the Cu and the transition metal is within 15-49 atomic percent, and a relationship of Ti, Cu, Zr and the transition metal is represented as $Ti_xCu_yZr_zQ_aR_b$,
Q being one or a plurality of Nb and Ta;
R being one or a plurality of Pd, and Co;
x being within a range of 40-70 atomic percent;
y being within a range of 10-30 atomic percent;
z being within a range of 4-10 atomic percent;
a being within a range of 5-7 atomic percent; and
b being within a range of 6-33 atomic percent.

2. The metal alloy powder of claim 1, having a relationship of Ti, Zr, Pd, Cu, Co and Ta represented as $Ti_{44}Zr_{10}Pd_{10}Cu_{6+x}Co_{23-x}Ta_7$, wherein x is within a range of 0-8 atomic percent.

3. The metal alloy powder of claim 1, wherein a fabrication of a biocompatible and antimicrobial bulk metallic glass from the metal alloy powder being an additive manufacturing.

4. The metal alloy powder of claims 1, wherein a fabrication of the biocompatible and antimicrobial bulk metallic glass involving laser-based rapid solidification.

5. The metal alloy powder of claim 1, a biocompatible and antimicrobial bulk metallic glass produced from the metal alloy powder having one or a plurality of the following structures comprising Ti and Cu: fully amorphous microstructure; amorphous and beta Ti phase; amorphous and elemental Cu phase; and amorphous and $(Ti,M)_2Cu$ phase, M being an alloying element.

6. The metal alloy powder of claim 1 which is pre-alloyed powder consisting of a plurality of particles, each one having the same composition and particle size of 10-100 μm.

7. The metal alloy powder of claim 1 which is pre-mixed powder consisting of a plurality of blended elemental particles, the mean composition of the homogeneously blended powder being within the said alloy composition, but the adjacent particles may have variation in their compositions and sizes.

8. A Ti-based metal alloy powder, consisting of:
Ti;
Cu within a range of 5-30 atomic percent;
Zr within a range of 4-35 atomic percent; and
transition metal within a range of 0-40 atomic percent,
wherein such transition metal is one or a plurality of Nb, Ta, Pd, and Co, a combined range of the Cu and the transition metal is within 20-49 atomic percent, and a relationship of Ti, Cu, Zr and the transition metal is represented as $Ti_xCu_yZr_zQ_aR_b$,
Q being one or a plurality of Nb and Ta;
R being one or a plurality of Pd, and Co;
x being within a range of 40-70 atomic percent;
y being within a range of 10-30 atomic percent;
z being within a range of 4-10 atomic percent;
a being within a range of 5-7 atomic percent; and
b being within a range of 6-33 atomic percent.

* * * * *